US 7,659,079 B2

(12) United States Patent
Estey et al.

(10) Patent No.: US 7,659,079 B2
(45) Date of Patent: Feb. 9, 2010

(54) TRANSMISSIBLE SPONGIFORM ENCEPHALOPATHY TEST REAGENTS AND METHODS

(75) Inventors: Lisa Ann Estey, Westbrook, ME (US); Reet Toomik, Uppsala (SE)

(73) Assignee: IDEXX Laboratories, Inc., Westbrook, ME (US)

( * ) Notice: Subject to any disclaimer, the term of this patent is extended or adjusted under 35 U.S.C. 154(b) by 434 days.

(21) Appl. No.: 11/099,128

(22) Filed: Apr. 5, 2005

(65) Prior Publication Data

US 2005/0239139 A1   Oct. 27, 2005

Related U.S. Application Data

(60) Provisional application No. 60/559,815, filed on Apr. 5, 2004.

(51) Int. Cl.
*A61K 31/715* (2006.01)
*A61K 31/795* (2006.01)
*C08B 37/02* (2006.01)
*G01N 33/53* (2006.01)

(52) U.S. Cl. .................. 435/7.1; 424/78.35; 435/7.8; 436/86; 514/59; 536/51

(58) Field of Classification Search .................. None
See application file for complete search history.

(56) References Cited

FOREIGN PATENT DOCUMENTS

| WO | 9830909 | 7/1998 |
|---|---|---|
| WO | 9941280 | 8/1999 |
| WO | 03/073106 | 4/2003 |

OTHER PUBLICATIONS

Pergami et al. *Biochem. Biophys. Res. Comm.*, vol. 264, pp. 972-978, 1999.*
Irvine et al, Molecular Med., vol. 14, 2008, pp. 451-464.*
Serban, et al., "Rapid detection of Creutzfeldt-Jakob disease and scrapie prion proteins", *Neurology*, 40, p. 110-117, (1990).
Brimacombe, et al., "*Characterization and polyanion-binding properties of purified recombinant prion protein*", Biochem J., (1999) 342, 605-613.
Notification of International Search Report dated Nov. 18, 2005 for corresponding PCT application International application No. PCT/US2005/011826.

* cited by examiner

*Primary Examiner*—Jeffrey Stucker
*Assistant Examiner*—Stephen Gucker
(74) *Attorney, Agent, or Firm*—McDonnell Boehnen Hulbert & Berghoff LLP

(57) ABSTRACT

The invention provides improved methods and compositions for selectively binding and/or detecting an aggregating abnormal form of a protein in the presence of non-aggregating normal form of the protein.

35 Claims, 11 Drawing Sheets

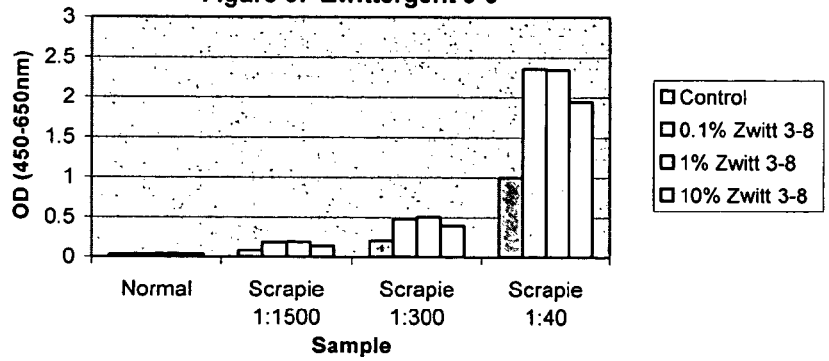
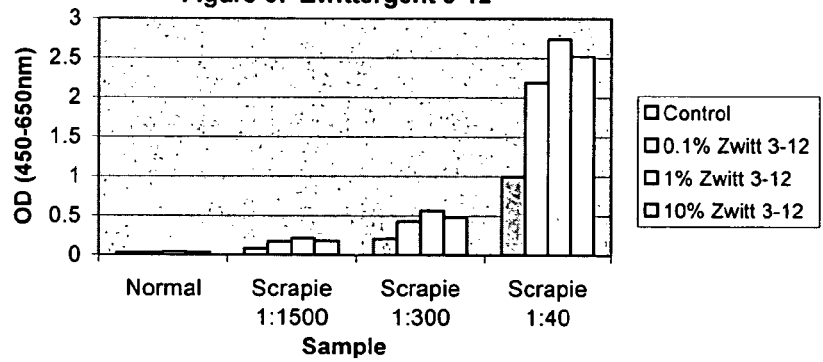
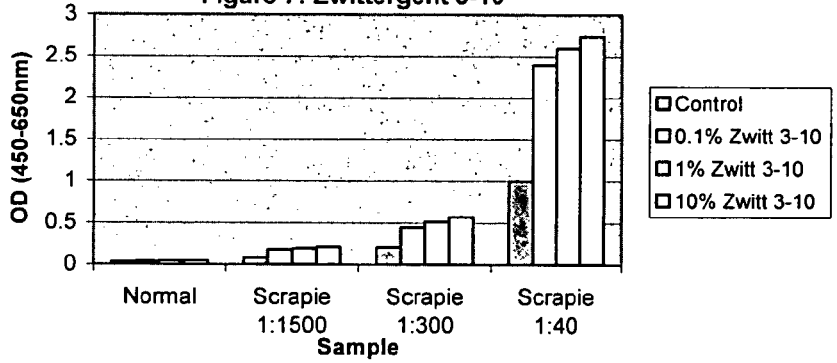
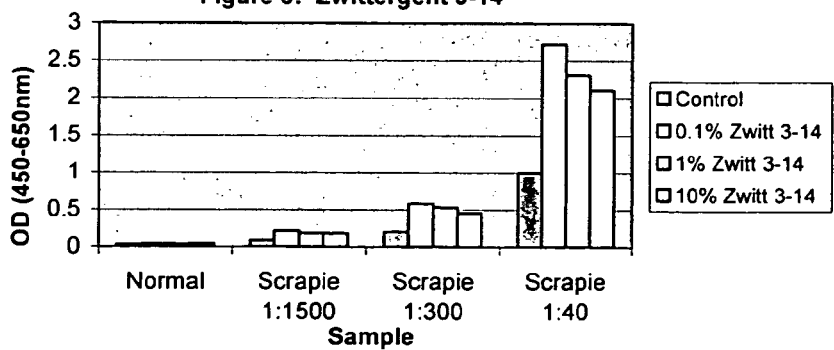

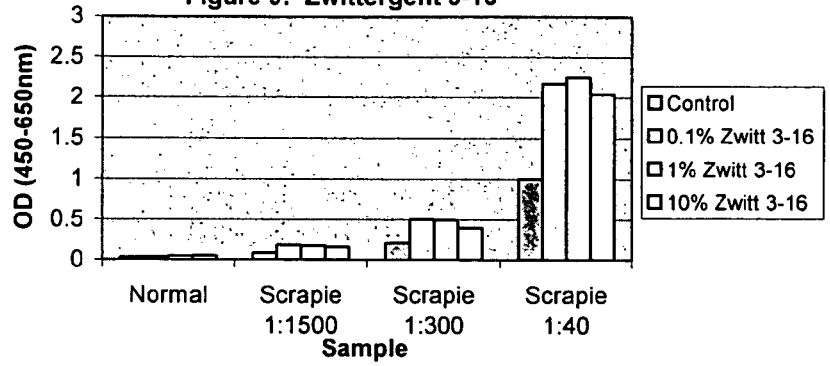
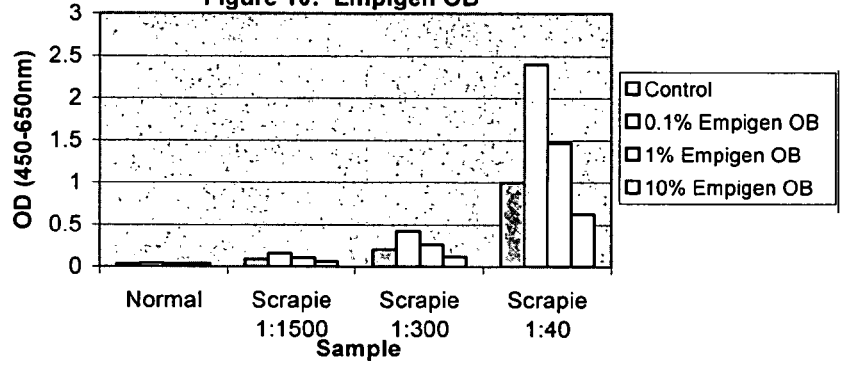
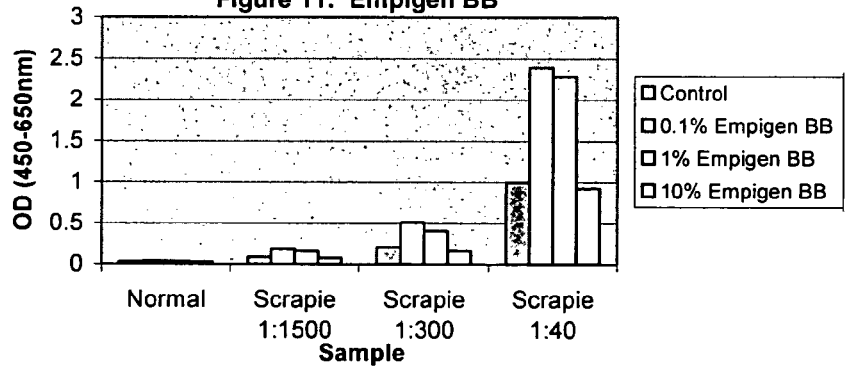
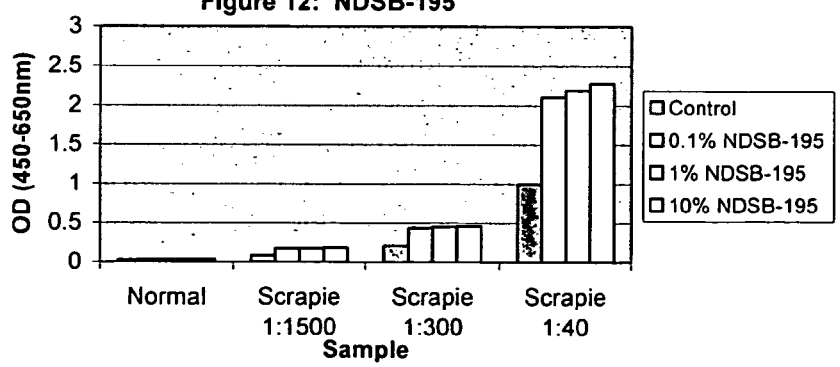

Figure 13: NDSB-201

Figure 14: NDSB-221

Figure 15: NDSB-256

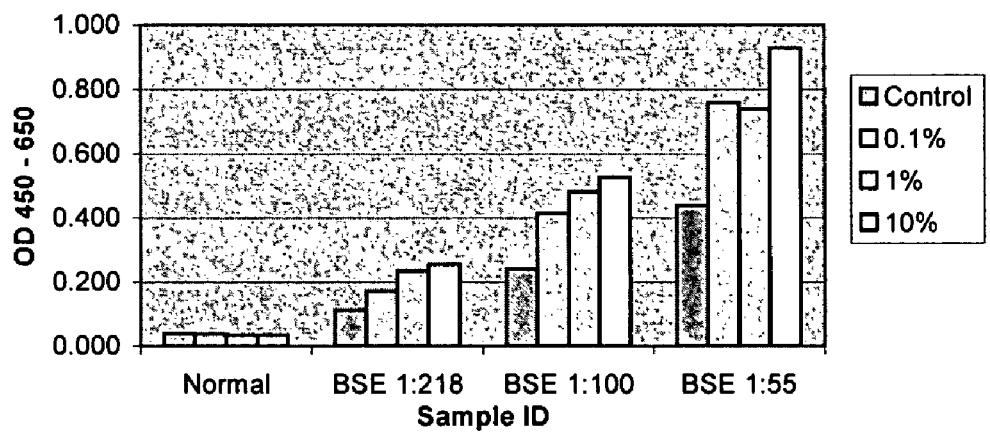
Figure 16: Zwittergent 3-8
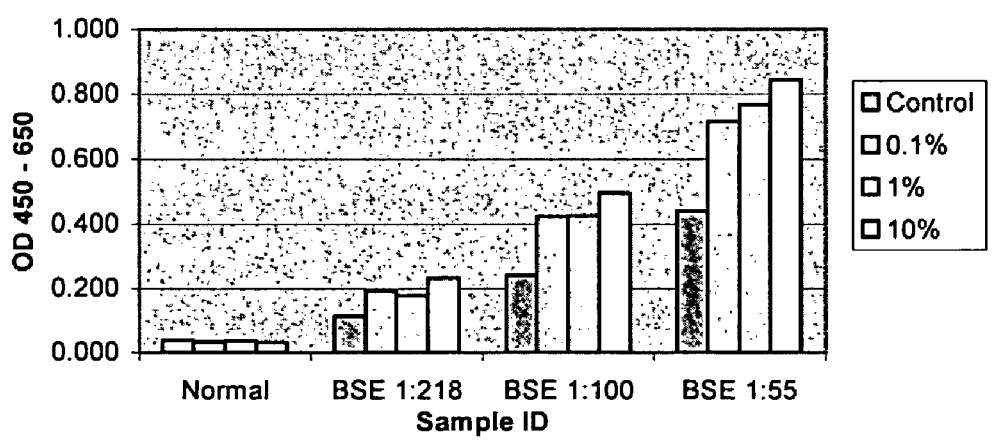
Figure 17: Zwittergent 3-10

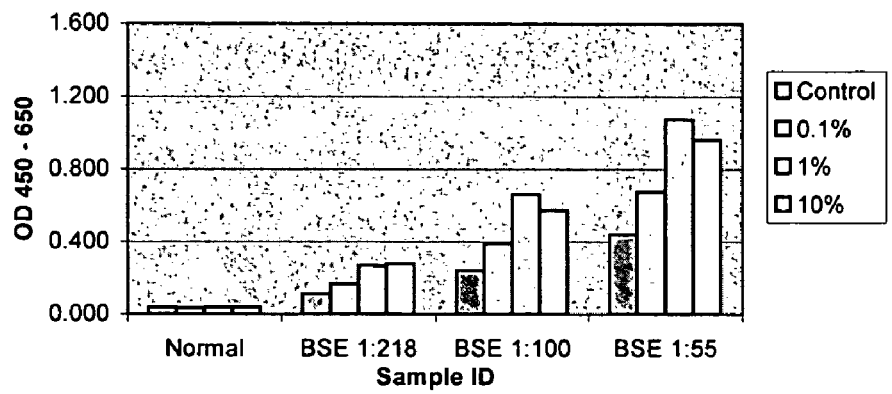
Figure 18: Zwittergent 3-12
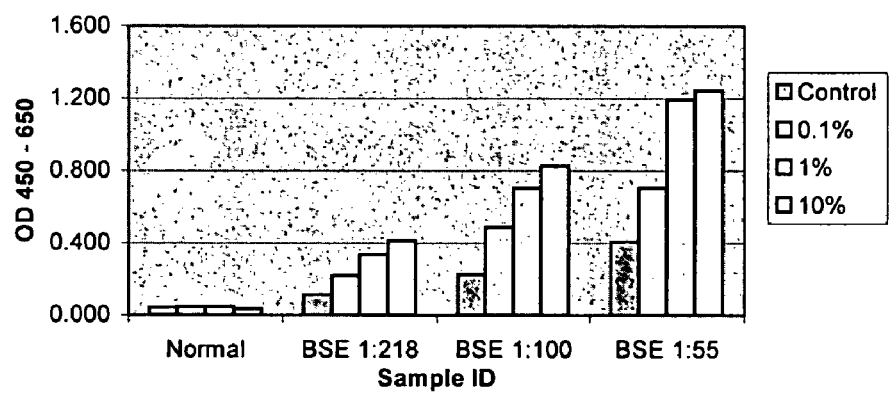
Figure 19: Zwittergent 3-14
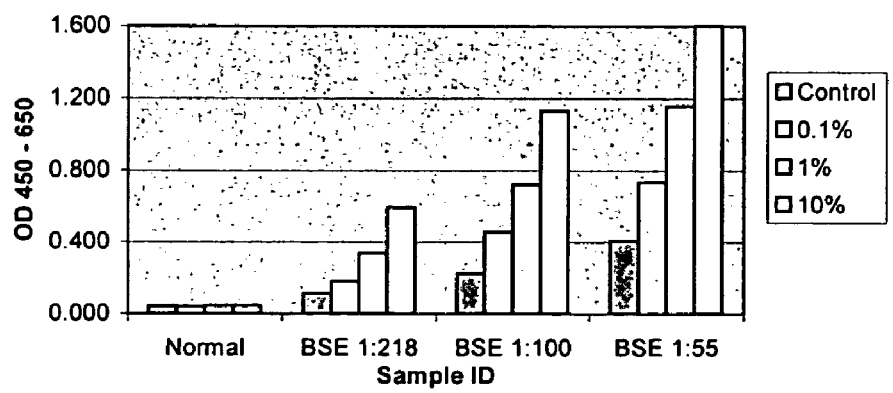
Figure 20: Zwittergent 3-16

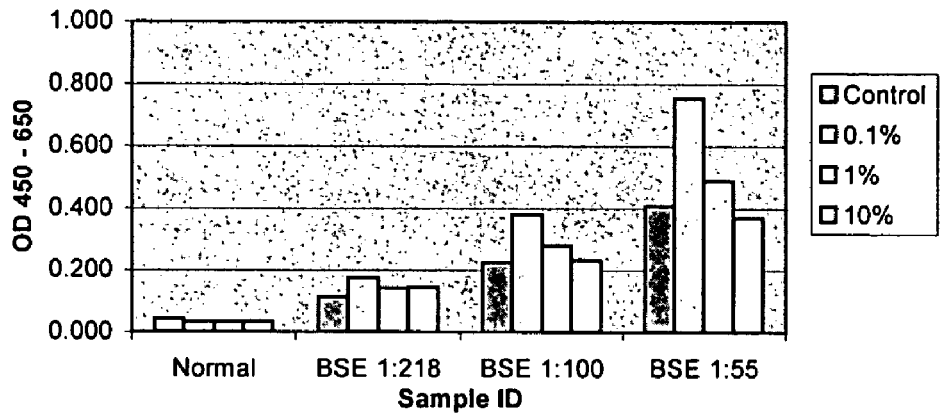
Figure 21: Empigen BB
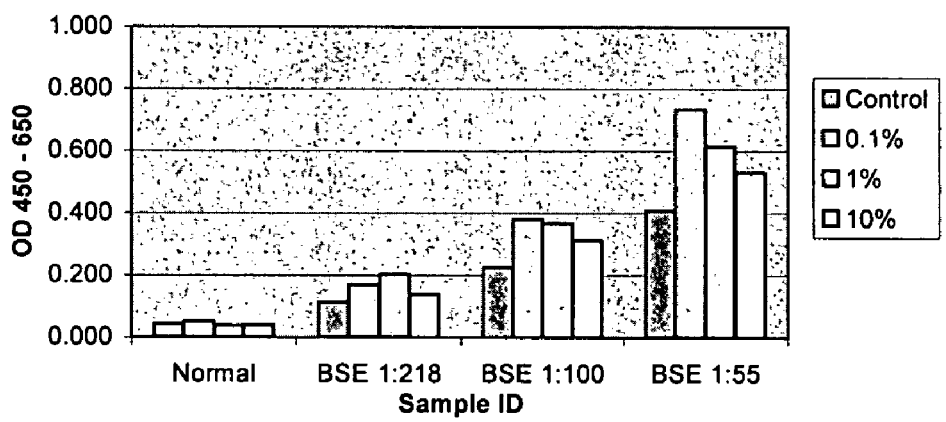
Figure 22: Empigen OB
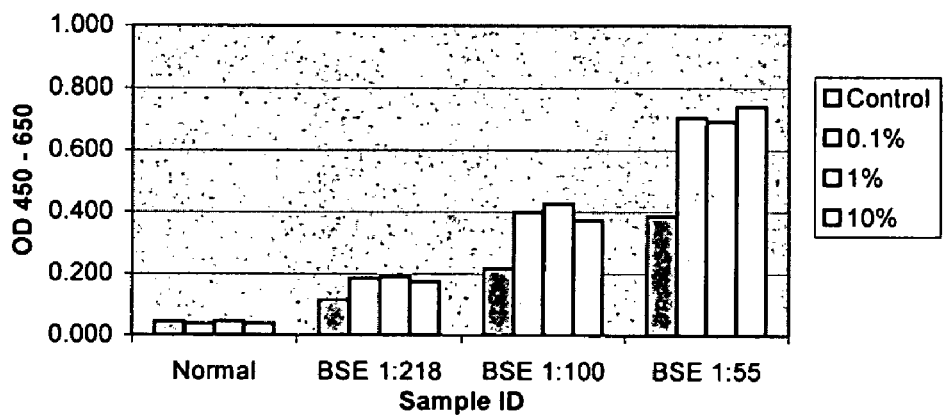
Figure 23: NSDB 195

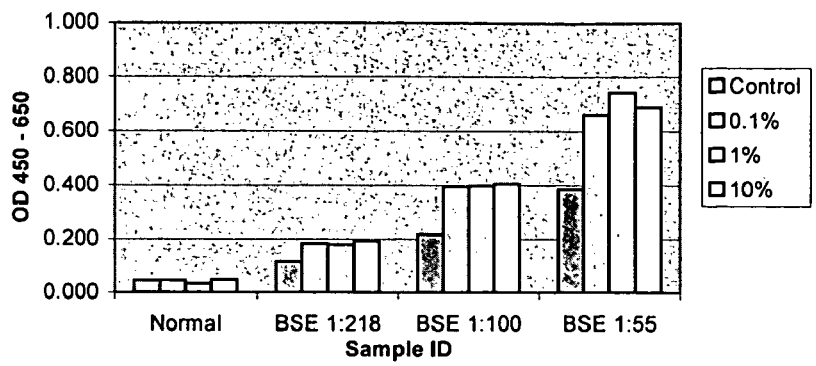
Figure 24: NSDB 201
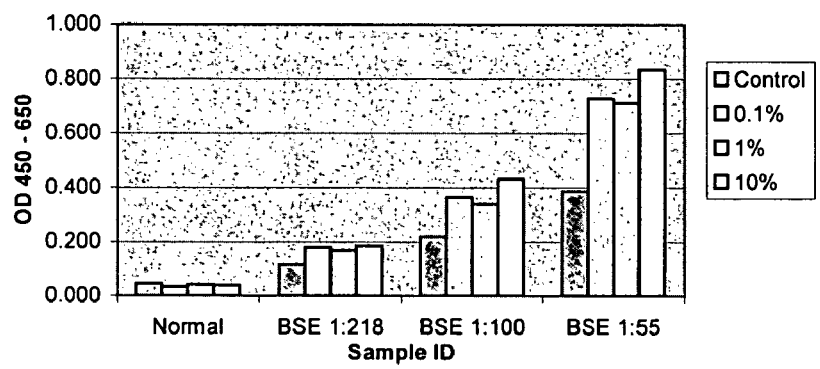
Figure 25: NSDB 221
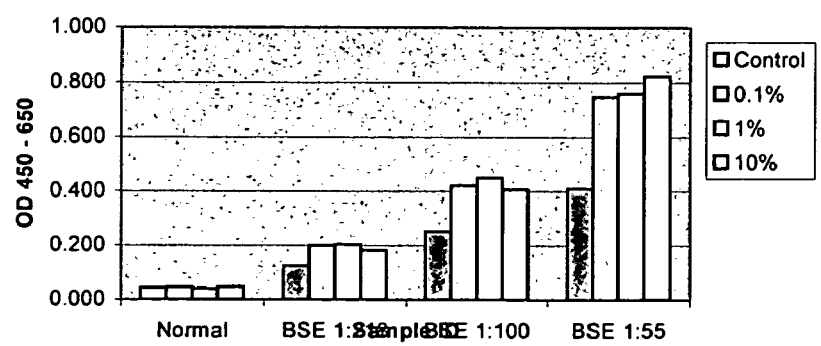
Figure 26: NSDB 256

TRANSMISSIBLE SPONGIFORM ENCEPHALOPATHY TEST REAGENTS AND METHODS

BACKGROUND OF THE INVENTION

Transmissible spongiform encephalopathies (TSEs) cause spongy degeneration of the brain with severe and fatal neurological symptoms in humans and animal. TSEs include scrapie, which affects sheep and goats; bovine spongiform encephalopathy (BSE), which affects cattle; transmissible mink encephalopathy; feline spongiform encephalopathy; chronic wasting disease (CWD) of cervids including mule deer, white-tailed deer, black-tailed deer, and elk; and kuru, Creutzfeldt-Jakob disease, Gerstmann-Straussler syndrome, fatal familial insomnia, and variant Creutzfeldt-Jakob disease (vCJD), which affect humans.

The only identified component of the agent causing TSEs is $PrP^{Sc}$, an abnormal aggregating isoform of $PrP^c$. Current methods of detecting $PrP^{Sc}$ subject a sample to proteolysis with proteinase K to destroy $PrP^c$. The presence of surviving $PrP^{Sc}$ is then determined by an immunoassay using an antibody that is not selective for $PrP^{Sc}$ in the presence of $PrP^c$. See Serban et al., Neurology, 40:110 1990. This methodology excludes the use of an antibody for capture or detection during the proteolysis step. Proteinase K must be removed or deactivated before any antibodies can be introduced to the assay.

Methods are needed that can rapidly identify samples containing TSEs with minimal sample handling, discriminate between the normal and disease-associated conformer of Prp independent of proteinase K digestion, and that can be automated for high throughput applications.

SUMMARY OF THE INVENTION

One embodiment of the invention provides a method for selective binding of an aggregating abnormal form of a protein in the presence of a non-aggregating normal form of the protein. The method comprises contacting, under selective binding conditions, brain tissue suspected of comprising the aggregating abnormal form and the non-aggregating normal form of the protein with a polyionic material having a binding avidity for the abnormal aggregating form of the protein, a zwitterionic agent, and a discriminating agent, wherein the aggregating abnormal form of the protein selectively binds to the polyionic material. The polyionic material can be protease resistant.

The polyionic material can be a polyanionic material having a multiplicity of anionic groups or a polycationic material having a multiplicity of cationic groups. The polyionic material can have a multiplicity of anionic groups that are sulphate, carboxyl or phosphate groups or a multiplicity of cationic groups that are amino groups, imine groups or quaternary ammonium groups.

The discriminating agent can have a lesser density of anionic groups than the polyionic material. The discriminating agent can be an anionic detergent or an amino acid amide of a fatty acid such as laurylsarcosine.

The aggregated abnormal form of the protein that is selectively bound to the polyionic material can be captured with an immobilized capture agent. The capture agent can be an antibody specific for the aggregated abnormal form of the protein.

The polyionic material which is selectively bound to the aggregated abnormal form of the protein can be captured with an immobilized capture agent. The capture agent can be a lectin or an antibody.

The selective binding conditions can comprise a pH from about 8 to about 9 or from about 8.2 to about 8.6.

The polyionic material can comprise a selectively bindable tag moiety and the capture agent can selectively bind to the tag moiety. The aggregated abnormal form of the protein comprises a selectively bindable tag moiety and the capture agent selectively binds to the tag moiety. The bindable tag moiety can be biotin, fluorescein, dinitrophenol, digoxyrenin, a nucleic acid or nucleic acid analogue sequence or (His) 6.

The polyionic material can be immobilized to a solid support material prior to contacting the brain tissue. The solid support material can have the polyionic material coated thereon. The polyionic material can be immobilized on the solid support through direct adsorption to the support. The polyionic material can comprise a selectively bindable tag moiety and can be immobilized to the solid support material via the tag moiety. The bindable tag moiety can be biotin, fluorescein, dinitrophenol, digoxyrenin, a nucleic acid or nucleic acid analogue sequence or (His) 6. The polyionic material can be a solid that provides a surface having said binding avidity.

The zwitterionic agent can comprise a zwitterionic detergent. The zwitterionic agent can comprise 3-(N,N-Dimethylocyl-ammonio) propanesulfonate, 3-(Decyldimethylammonio) propanesulfonate, 3-(Dodecyldimethylammonio) propanesulfonate, 3-(N,N-Dimethylmyristylammonio) propanesulfonate, 3-(N,N-Dimethylpalmitylammonio) propanesulfonate, n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, n-tetradecyl-N,N-dimethyl-3-ammonio-1-propanesulfonate, n-Hexadecyl-N,N-dimethyl-3-ammonio-1-propanesulfonate, a sulfobetaine, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate n-dodecyl-N, N-dimethylglycine, lauryldimethylamine oxide, or combinations thereof. The zwitterionic agent can comprise a sulfobetaine. The zwitterionic agent can comprise a sulfonate group or a carboxyl group. The abnormal aggregated form of the protein can be $PrP^{Sc}$ and the non-aggregated normal form of the protein can be $PrP^c$.

Another embodiment of the invention provides a method of determining presence or absence of an abnormal aggregating form of a protein in a brain tissue sample in the presence of the non-aggregating normal form of the protein. The method comprises contacting, under selective binding conditions, brain tissue suspected of comprising the aggregating abnormal form of the protein and the non-aggregating normal form of the protein with a polyionic material having a binding avidity for the abnormal aggregating form of the protein, a discriminating agent and a zwitterionic agent; and determining the presence or absence of the abnormal aggregating form of the protein bound to the polyionic material.

The amount of the abnormal aggregating form of a protein can be determined. Determining the presence or absence of the abnormal aggregating form of the protein bound to the polyionic material can be qualitatively or quantitatively determined by conducting an immunoassay for the aggregating form of the protein.

The abnormal aggregated form of the protein can be $PrP^{Sc}$ and the non-aggregated normal form of the protein can be $PrP^{c}$.

The zwitterionic agent can comprise a zwitterionic detergent. The zwitterionic agent can comprise 3-(N,N-Dimethylocyl-ammonio) propanesulfonate, 3-(Decyldimethylammonio) propanesulfonate, 3-(Dodecyldimethylammonio) propanesulfonate, 3-(N,N-Dimethylmyristylammonio) propanesulfonate, 3-(N,N-Dimethylpalmitylammonio) propanesulfonate, n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, n-tetradecyl-N,N-dimethyl-3-ammonio-1-propanesulfonate, n-Hexadecyl-N,N-dimethyl-3-ammonio-1-propanesulfonate, a sulfobetaine, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate n-dodecyl-N, N-dimethylglycine, lauryldimethylamine oxide, or combinations thereof. The zwitterionic agent can comprise a sulfobetaine. The zwitterionic agent can comprise a sulfonate group or a carboxyl group.

BRIEF DESCRIPTION OF THE DRAWINGS

FIG. 5 shows the effect of ZWITTERGENT® 3-8 in plate diluent 1 on a scrapie EIA.

FIG. 6 shows the effect of ZWITTERGENT® 3-12 in plate diluent 1 on a scrapie EIA.

FIG. 7 shows the effect of ZWITTERGENT® 3-10 in plate diluent 1 on a scrapie EIA.

FIG. 8 shows the effect of ZWITTERGENT® 3-14 in plate diluent 1 on a scrapie EIA.

FIG. 9 shows the effect of ZWITTERGENT® 3-16 in plate diluent 1 on a scrapie EIA.

FIG. 10 shows the effect of EMPIGEN® OB in plate diluent 1 on a scrapie EIA.

FIG. 11 shows the effect of EMPIGEN® BB in plate diluent 1 on a scrapie EIA.

FIG. 12 shows the effect of NDSB-195 in plate diluent 1 on a scrapie EIA.

Figures 13, 14, 15:
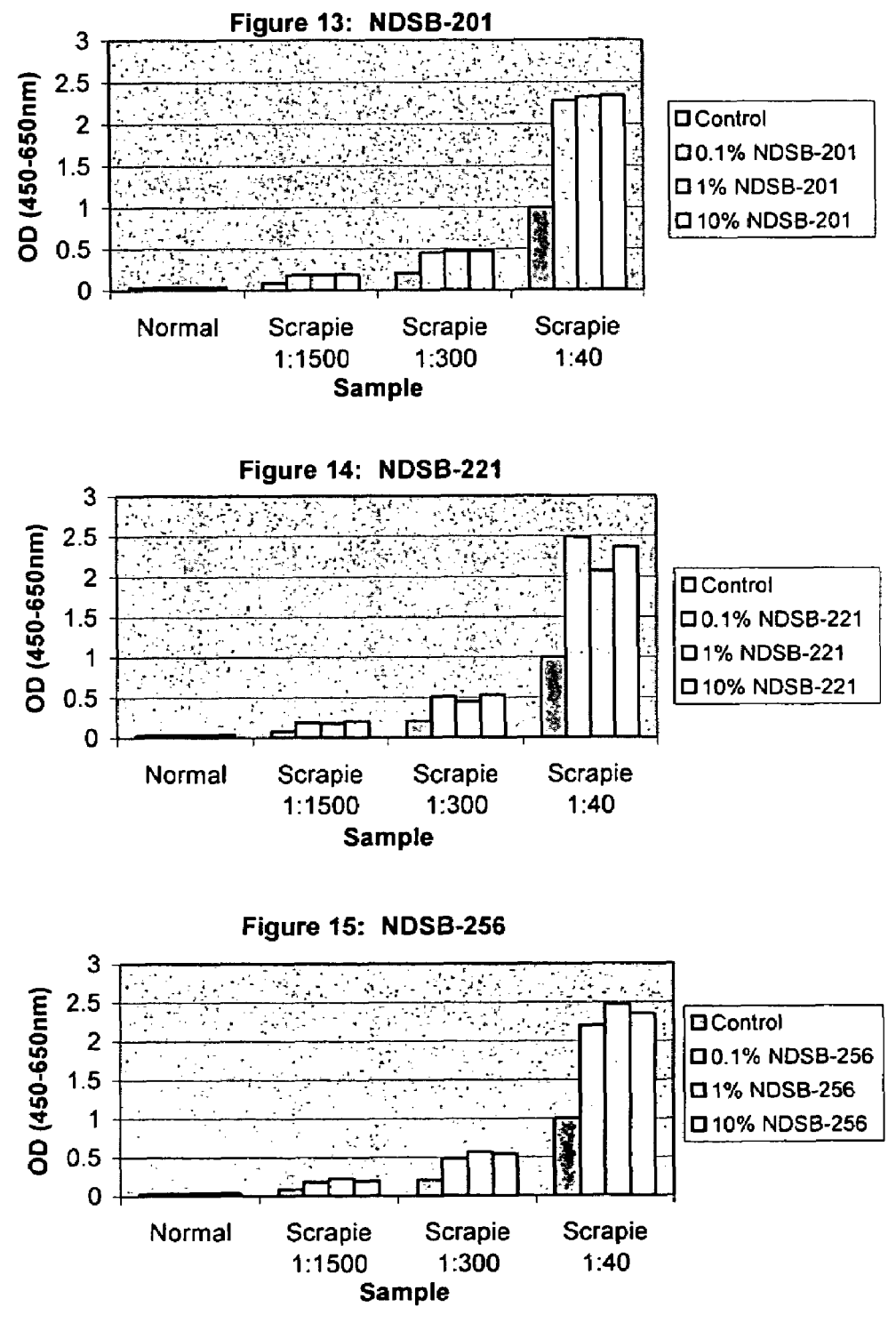

FIG. 13 shows the effect of NDSB-201 in plate diluent 1 on a scrapie EIA.

FIG. 14 shows the effect of NDSB-221 in plate diluent 1 on a scrapie EIA.

FIG. 15 shows the effect of NDSB-256 in plate diluent 1 on a scrapie EIA.

FIG. 16 shows the effect of ZWITTERGENT® 3-8 in plate diluent 1 on a BSE EIA.

FIG. 17 shows the effect of ZWITTERGENT® 3-12 in plate diluent 1 on a BSE EIA.

FIG. 18 shows the effect of ZWITTERGENT® 3-10 in plate diluent 1 on a BSE EIA.

FIG. 19 shows the effect of ZWITTERGENT® 3-14 in plate diluent 1 on a BSE EIA.

FIG. 20 shows the effect of ZWITTERGENT® 3-16 in plate diluent 1 on a BSE EIA.

FIG. 21 shows the effect of EMPIGEN® OB in plate diluent 1 on a BSE EIA.

FIG. 22 shows the effect of EMPIGEN® BB in plate diluent 1 on a BSE EIA.

FIG. 23 shows the effect of NDSB-195 in plate diluent 1 on a BSE EIA.

FIG. 24 shows the effect of NDSB-201 in plate diluent 1 on a BSE EIA.

FIG. 25 shows the effect of NDSB-221 in plate diluent 1 on a BSE EIA.

FIG. 26 shows the effect of NDSB-256 in plate diluent 1 on a BSE EIA.

Figure 1:
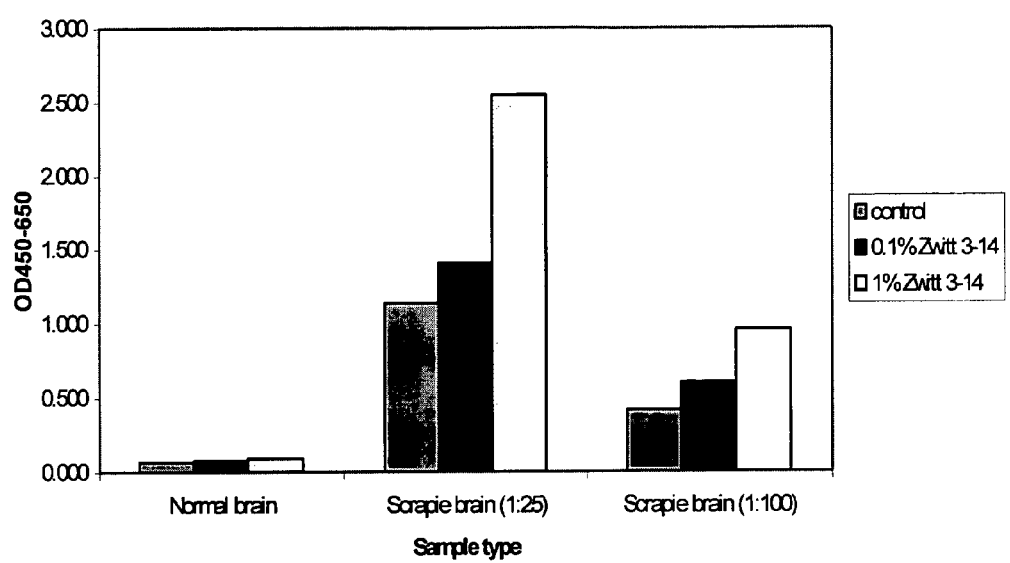
FIG. 1 demonstrates that addition of ZWITTERGENT® 3-14 (n-tetradecyl-N,N-dimethyl-3-ammonio-1-propanesulfonate) to the working plate diluent improves detection of ovine brain $PrP^{Sc}$.

DETAILED DESCRIPTION OF THE INVENTION

It has recently been discovered that selective binding of an aggregating abnormal form of a protein can be achieved by contacting a sample containing both aggregating abnormal forms of a protein and non-aggregating normal forms of the protein, under selective binding conditions, with a polyionic material having a binding avidity for the aggregating abnormal form of the protein. See WO 03/073106 A2 (Lane et al., "Binding of Pathological Forms of Prion Proteins"), which is incorporated by reference herein in its entirety. The binding conditions can include a discriminating agent such as laurylsarcosine. Among the advantages to this method is the fact that the proteolysis step is eliminated. Therefore, antibodies or other proteins can be added to the selective binding conditions at any time. The polyionic materials, selective binding conditions, other conditions, other materials, assay methods, and other methods described in WO 03/073106 can be used in the instantly disclosed methods and are specifically incorporated by reference in their entirety herein.

The instant invention provides an improvement to the compositions and methods described in WO 03/073106. The improvement comprises addition of a charged agent, such as charged detergent agent, for example, a zwitterionic agent to the selective binding conditions.

For example, brain tissue comprising an aggregating abnormal form of a protein and a non-aggregating normal form of the protein can be contacted, under selective binding conditions, with a polyionic material having a binding avidity for the abnormal aggregating form of the protein, a zwitterionic agent, and a discriminating agent such as laurylsarcosine.

Selective binding means that an aggregating abnormal form of a protein binds to a polyionic material having a binding avidity for the aggregating abnormal form of the protein, while the non-aggregating abnormal form of the protein does not substantially bind the polyionic material.

Selective binding conditions provide conditions under which polyionic materials bind aggregated abnormal proteins forms, for example, $PrP^{Sc}$, but do not substantially bind the non-aggregated normal form of the protein, for example $PrP^{c}$. Selective binding conditions provide binding that is sufficiently strong and selective to be useful in assays for the presence of the aggregated abnormal form of the protein. Selective binding conditions can be determined by one of skill in the art and can be obtained by, for example, suitable adjustment of the reaction conditions, particularly the presence and concentration of a discriminating agent, a charged agent such as a zwitterionic agent, the pH, and the detergency. Suitable selective binding conditions are described in, for example, WO 03/073106 and in the examples below. In one embodiment of the invention selective binding conditions comprise a pH from about 8 to about 9, and more particularly a pH from about 8.2 to about 8.6.

Binding avidity means the overall binding strength of a molecule with many binding sites with a multivalent binding agent (e.g., the polyionic material), which is in contrast to "affinity", which is the binding strength between each individual binding site of the molecule and the binding agent (e.g., the polyionic material).

Suitable polyionic materials having a binding avidity for the aggregating abnormal form of the protein are described in WO 03/073106, which is incorporated by reference herein in its entirety. A polyionic material can be protease resistant. The polyionic material can be a polyanionic material having a multiplicity of anionic groups or a polycationic material having a multiplicity of cationic groups. Anionic groups can be, for example, sulphate, carboxyl or phosphate groups. Cationic groups can be, for example, amino groups, imine groups or quaternary ammonium groups.

In one embodiment of the invention a detergent is part of the selective binding conditions and promotes selective binding either by virtue of detergency or by acting as a discriminating agent.

Aggregating Abnormal and Non-Aggregating Normal Forms of Proteins

Methods of the invention can detect or selectively bind an aggregating abnormal form of a protein in the presence of the non-aggregating normal form of the protein. In particular, methods of the invention can detect or selectively bind an aggregating abnormal form of a protein in the presence of a non-aggregating normal form of the protein wherein the proteins are present in or derived from brain tissue. The methods of the invention comprise contacting, under selective binding conditions, a sample, such as brain tissue, suspected of comprising the aggregating abnormal form and the non-aggregating normal form of the protein, with a polyionic material having a binding avidity for the abnormal aggregating form of the protein, a zwitterionic agent, and a discriminating agent such as laurylsarcosine.

One example of a protein that has aggregating abnormal forms and non-aggregating normal forms is PrP. The only identified component of the agent that causes transmissible spongiform encephalopathies (TSEs) is $PrP^{Sc}$, which is an abnormal aggregating isoform of the non-aggregating normal form of $PrP^{c}$. Therefore, in one embodiment of the invention, the disclosed methods can be used to detect or selectively bind $PrP^{Sc}$ in the presence of $PrP^{c}$.

One example of aggregating abnormal forms of proteins are abnormal protein aggregates dominated by beta-sheet structures such as beta-peptides that form amyloid deposits in Alzheimer's disease, alpha-synuclein protein that produces amyloid-like deposits in Lewy bodies of Alzheimer's and Parkinson's patients, and the ABri peptide that form amyloid deposits in familial British dementia (FBD).

The test samples can be, for example, mammalian brain tissue. In one embodiment of the invention the obex is used. Methods of the invention can detect or selectively bind TSEs in samples suspected of comprising TSEs that cause scrapie, BSE, transmissible mink encephalopathy, feline spongiform encephalopathy, CWD, kuru, Creutzfeldt-Jakob disease, Gerstmann-Straussler syndrome, fatal familial insomnia, and variant Creutzfeldt-Jakob disease (vCJD).

Charged Detergent Agents

A charged detergent or detergent-like agent can be added to the selective binding conditions of the methods of the invention to improve sensitivity and detection of an aggregating abnormal form of a protein. A charged detergent or detergent-like agent can be an anionic, cationic, or zwitterionic detergent or detergent-like agent. A zwitterionic agent is a molecule carrying both a positive and a negative charge. Any zwitterionic agent can be used in the methods of the invention, for example, a zwitterionic agent can be, for example, ZWITTERGENT® 3-08 (n-Octyl-N,N-dimethyl-3-ammonio-1-propanesulfonate), ZWITTERGENT® 3-10 (n-Decyl-N,N-dimethyl-3-ammonio-1-propanesulfonate), ZWITTERGENT® 3-12 (n-Dodecyl-N,N-dimethyl-3-ammonio-1-propanesulfonate), ZWITTERGENT® 3-14 (n-tetradecyl-N,N-dimethyl-3-ammonio-1-propanesulfonate), ZWITTERGENT® 3-16 (n-Hexadecyl-N,N-dimethyl-3-ammonio-1-propanesulfonate). In one embodiment of the invention the zwiterionic compound is a Zwitterionic detergent.

Other zwitterionic agents are sulfobetaines, including, for example, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate. Other zwitterionic agents include n-dodecyl-N,N-dimethylglycine, and lauryldimethylamine oxide. See also, the zwitterionic agents listed in Examples 2 and 3.

About 0.1% to about 10% of a charged agent, such as a zwitterionic agent is added to the selective binding stock solution or working plate diluent. Therefore, about 0.02, 0.05, 0.1, 0.5, 1.0, 1.5, 2.0, 3.0, 4.0, 5.0, 6.0, 7.0, 8.0, 9.0, 10, 15, or 20% of a zwitterionic agent is present in a selective binding reaction.

Discriminating Agents

A discriminating agent is an agent that allows selective binding of $PrP^{Sc}$ to a polyionic material, as described above, and/or prevents $PrP^{c}$ from binding to the polyionic material. The discriminating agent can have a lesser density of anionic groups than the polyionic material. The discriminating agent can be an anionic detergent, an amino acid amide of a fatty acid, or laurylsarcosine. A discriminating agent can comprise about 0.5, 1.0, 2.0, 3.0, 4.0, 5.0, or 10% of the selective binding conditions.

Detection of Aggregating Abnormal Forms of a Protein

Once the aggregating abnormal form of the protein has been selectively bound to the polyionic material and optionally after the normal form of the protein has been removed, the presence or absence and/or quantity of the aggregating abnormal form the protein can be determined. See e.g., WO 03/073106. Any assay type to detect the selectively bound abnormal form of the protein can be used. For example, enzyme linked immunosorbent assay (ELISA), western blot, indirect fluorescent antibody assay (IFA), radioimmunoassay (RIA), hemagglutination (HA), and fluorescence polarization immunoassay (FPIA) can be used. Any antibody specific for PrP can be used in these assays. Several of such antibodies are known in the art. In some cases, a denaturant, such as guanidine thiocyanate (GuSCN), is used to expose PrP epitopes before or during the addition of an antibody specific for PrP to the assay.

The polyionic material can be immobilized to a solid support material either before or after being contacted with a sample. Separation of the sample from the solid support material can then be used to remove the non-aggregating normal form of the protein from the assay leaving only the aggregated abnormal of the protein. Solid support materials are well known in the art and include, for example, include microtiter plates, dipsticks, laminar flow devices, microbeads and superparamagnetic microbeads.

Biotin or other tags can be conjugated to the polyionic material by methods well known in the art. Biotin is a bindable tag moiety that can be used to bind the polyionic material to a solid support material derivatized with avidin or a material with avidin binding properties such as steptavidin, Neutravidin or Captavidin.

Other molecules can be used as bindable tag moieties and include those that are readily conjugated to a polyionic material and that can be captured or bound by a suitable capture agent such as fluorescein dinitrophenol DNP, digoxygenin, nucleic acid or nucleic acid analog sequences, and (His) 6. A capture agent can be used that selectively binds the polyionic material itself rather than through a tag moiety. For instance, polyglycosides can be bound by a suitable lectin or by a suitable antibody.

The captured aggregating abnormal form of the protein can be, if necessary, eluted from the polyionic material prior to the assay. Sodium dodecyl sulphate (SDS) is suitable for this purpose and is preferably used at a concentration of about 0.5 to about 1% by weight, preferably above about 0.75%.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above. All references cited in this disclosure are incorporated herein by reference.

EXAMPLES

Example 1

Brain samples (ovine or bovine) were collected from known negative or TSE-positive animals and homogenized to prepare 10-20% lysates in water. Before applying the homogenate to an ELISA assay plate, the sample was diluted into a working plate diluent, which is composed of plate diluent component 1 and plate diluent component 2. Plate diluent component 1 contains 250 mM TrisHCl, pH 8.3, 5% bovine serum albumin, 5% laurylsarcosine and 5% TRITON® X-100. Plate diluent component 2 (1 mg/ml DNAse I and 2.5 mg/ml trypsin) was mixed thoroughly with component 1, and 25 µl of the final working plate diluent was mixed with 100 µl of brain homogenate to prepare the sample for assay.

ELISA assays were performed using antigen capture plates that were coated with a charged polyionic polymer. See WO 03/073106. One hundred µls of brain homogenate-working plate diluent mixture were applied to each well and incubated for two hours at room temperature without agitation. After two hours, the lysates were aspirated from the plates, and the plates were washed 6 times with 1× wash solution. The last wash was aspirated, tapped on absorbent pad, and 100 µl of conditioning buffer containing 4M guanidine thiocyanate added to the wells. After a 10 minute incubation at room temperature, the plates were aspirated and washed 3 times with 1× wash solution.

To detect bound $PrP^{Sc}$, the plates were incubated with 100 µl of HRPO-conjugated anti-PrP antibody solution for one hour at room temperature. After aspiration of the detection antibody solution, the plates were washed 5 times with 1× wash solution. The plates were then tapped dry onto an absorbent pad, 100 µl of TMB substrate added, and the plates incubated for 15 minutes to allow color development. The assay was then stopped with an HCl stop solution, and absorbance of the microwells read at 450 nm and 650 nm (for background compensation).

To determine if the addition of ZWITTERGENT® 3-14 (n-tetradecyl-N,N-dimethyl-3-ammonio-1-propane-sulfonate) to the working plate diluent would improve the performance of the TSE assay, either 5% or 0.5% ZWITTERGENT® 3-14 (n-tetradecyl-N,N-dimethyl-3-ammonio-1-propanesulfonate) were added to the formulation for working plate diluent component 1. Assays were performed using normal sheep brain, or scrapie sheep brain homogenate that was diluted into normal sheep brain homogenate at either 1:25 or 1:100 ratios; the ELISA assay protocol used was the one described above. The results are shown in FIG. 1. In FIG. 1, control refers samples that were treated using a working plate diluent formulated with TRITON® X-100 (Alkylaryl polyether alcohol) and laurylsarcosine; 0.1% or 1% Zwitt 3-14 refers to formulations where either 0.5% or 5% ZWITTERGENT® 3-14 (n-tetradecyl-N,N-dimethyl-3-ammonio-1-propanesulfonate) (respectively) were added along with TRITON® X-100 (Alkylaryl polyether alcohol) and laurylsarcosine to the working plate diluent.

FIG. 1 shows that the addition of ZWITTERGENT® 3-14 (n-tetradecyl-N,N-dimethyl-3-ammonio-1-propane-sulfonate) to the working plate diluent does not affect the signal observed with normal brain samples, but with scrapie brain samples, the signal observed nearly doubled when ZWITTERGENT® 3-14 (n-tetradecyl-N,N-dimethyl-3-ammonio-1-propanesulfonate) was used at 5% as a supplement to the working plate diluent. These data suggest that the presence of ZWITTERGENT® 3-14 (n-tetradecyl-N,N-dimethyl-3-ammonio-1-propanesulfonate) at concentrations greater than 0.5% in the working plate diluent augment the $PrP^{Sc}$-specific signal captured from ovine brain homogenates using plates coated with a charged polyionic polymer.

Figure 2:
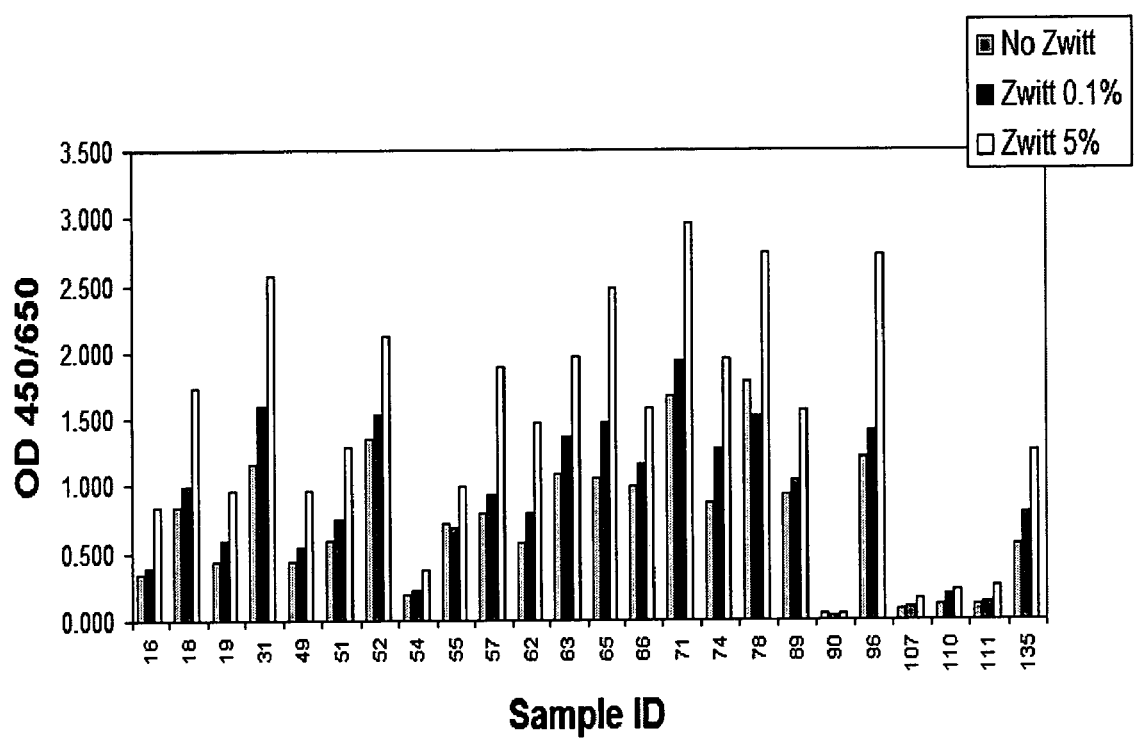
FIG. 2 demonstrates that addition of ZWITTERGENT® 3-14 (n-tetradecyl-N,N-dimethyl-3-ammonio-1-propanesulfonate) to the working plate diluent improves the detection of BSE.

FIG. 2 illustrates that ZWITTERGENT® 3-14 (n-tetradecyl-N,N-dimethyl-3-ammonio-1-propanesulfonate) is equally effective at enhancing the detection of $PrP^{Sc}$ derived from the brains of bovines affected by BSE. For the experiment in shown in FIG. 2, either 5% or 0.1% ZWITTERGENT® 3-14 (n-tetradecyl-N,N-dimethyl-3-ammonio-1-propanesulfonate) were added to the formulation for working plate diluent component 1. Assays were performed using several BSE brain homogenates (n=24); the assay protocol used is the one described above. In FIG. 2, no Zwitt refers samples that were treated using a working plate diluent formulated with TRITON® X-100 (Alkylaryl polyether alcohol) and laurylsarcosine; 0.1% or 5% refers to concentrations of ZWITTERGENT® 3-14 (n-tetradecyl-N,N-dimethyl-3-ammonio-1-propanesulfonate) added along with TRITON® X-100 (Alkylaryl polyether alcohol) and laurylsarcosine to the working plate diluent. As seen with the ovine brain samples, ZWITTERGENT® 3-14 (n-tetradecyl-N,N-dimethyl-3-ammonio-1-propanesulfonate) was effective at increasing the signal captured using polyionic polymer-coated plates in all but four BSE samples (whose $OD_{450-650}$ approached the assay cut-off).

Figure 3:
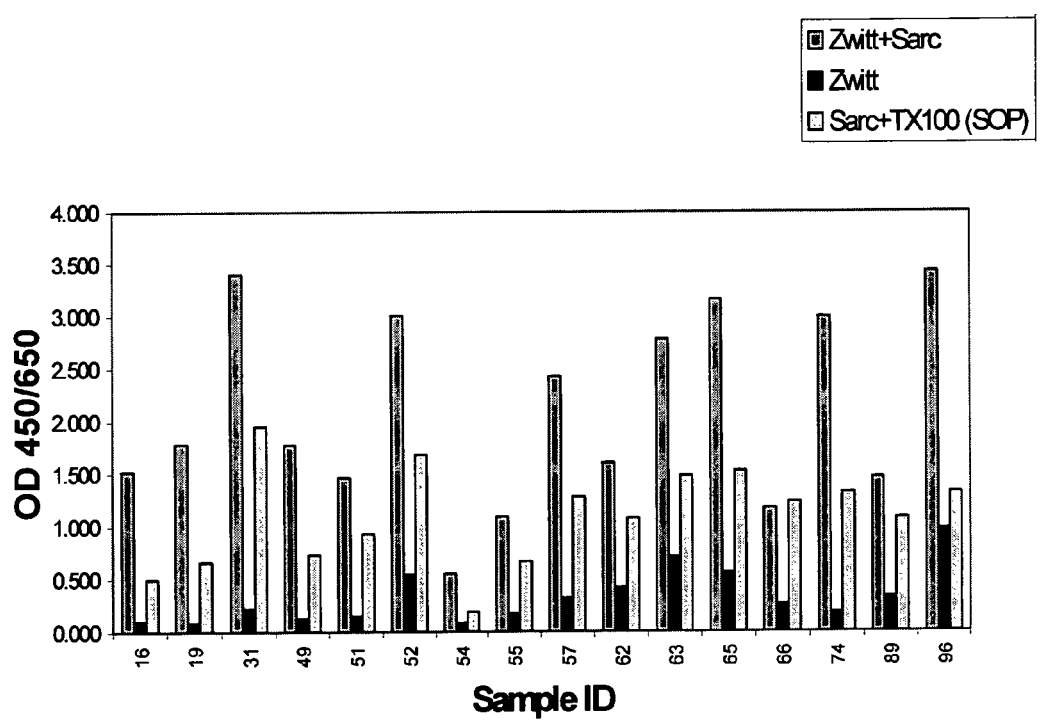
FIG. 3 demonstrates the working plate diluent detergent composition required for enhanced detection of $PrP^{Sc}$.

The experiments summarized in FIG. 3 investigate the conditions that are required for improved detection of $PrP^{Sc}$ in ELISA assays. In these experiments, plate diluent component 1 was prepared using 250 mM TrisHCl, pH 8.3 and 5% bovine serum albumin along with the following compositions: a) 5% ZWITTERGENT® 3-14 (n-tetradecyl-N,N-dimethyl-3-ammonio-1-propanesulfonate) and 5% laurylsarcosine, b) 5% ZWITTERGENT® 3-14 (n-tetradecyl-N,N-dimethyl-3-ammonio-1-propanesulfonate) alone, or c) 5% laurylsarcosine and 5% TRITON® X-100 (Alkylaryl polyether alcohol). In this study, BSE brain homogenates were tested using these formulations of plate diluent component 1 in the ELISA described above. Therefore, in this experiment, effective working plate diluent requires both laurylsarcosine and zwitterionic agent to show improved assay sensitivity.

The data in FIG. 3 clearly shows that using a zwitterionic detergent such as ZWITTERGENT® 3-14 (n-tetradecyl-N,N-dimethyl-3-ammonio-1-propanesulfonate) alone in the working plate diluent is ineffective. Replacing TRITON® X-100 (Alkylaryl polyether alcohol) with ZWITTERGENT® 3-14 (n-tetradecyl-N,N-dimethyl-3-ammonio-1-propanesulfonate) in the presence of laurylsarcosine, on the other hand, results in greater assay sensitivity than TRITON® X-100 (Alkylaryl polyether alcohol) and laurylsarcosine, with many of the samples doubling their $OD_{450-650}$ with this treatment.

Figure 4:
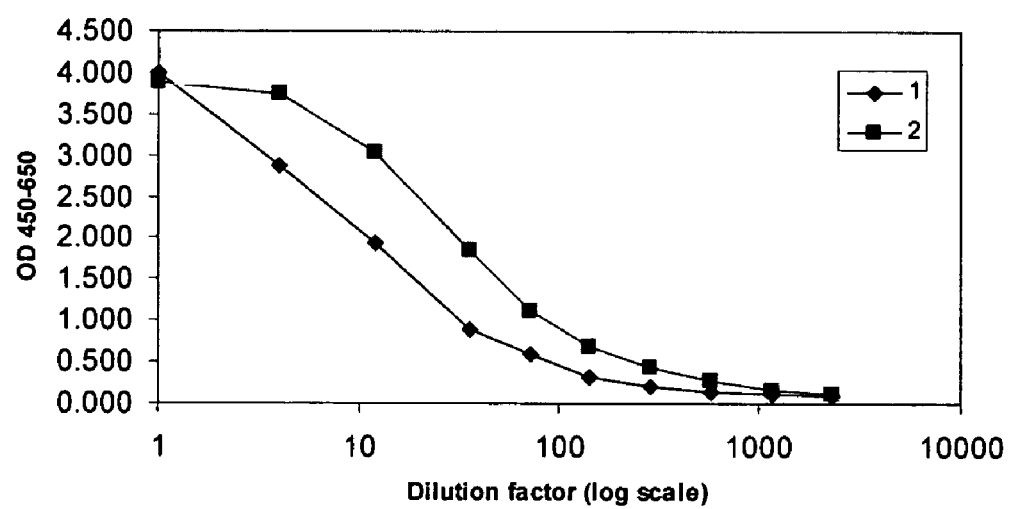
FIG. 4 demonstrates ELISA sensitivity in a sample dilution series.

To determine how the addition of ZWITTERGENT® 3-14 (n-tetradecyl-N,N-dimethyl-3-ammonio-1-propanesulfonate) to the working plate diluent influences the sensitivity of a BSE ELISA assay, a series of dilutions of BSE brain homogenate into normal bovine brain homogenate were prepared and tested with the working plate diluent. In FIG. 4, curve #1 represents a sample dilution run with the working plate diluent formulated with Tris buffer, bovine serum albumin, 5% TRITON® X-100 (Alkylaryl polyether alcohol) and 5% laurylsarcosine. Curve #2 represents the sample dilution run with working plate diluent in which TRITON® X-100 (Alkylaryl polyether alcohol) was substituted by 5% ZWITTERGENT® 3-14 (n-tetradecyl-N,N-dimethyl-3-ammonio-1-propanesulfonate). The data illustrates that substituting ZWITTERGENT® 3-14 (n-tetradecyl-N,N-dimethyl-3-ammonio-1-propanesulfonate) into the working plate diluent results in nearly a one log unit increase in the sensitivity. For the TRITON® X-100 (Alkylaryl polyether alcohol) diluent, the last dilution detected above the assay cut-off was 1:288, while for the ZWITTERGENT® 3-14 (n-tetradecyl-N,N-dimethyl-3-ammonio-1-propanesulfonate) formulation, the last dilution detected above the cut-off was between 1:576 and 1:1152.

Example 2

Evaluation of Different Zwitterionic Detergents in Plate Diluent

The addition of zwitterionic detergents to TSE EIA Plate Diluent 1 was investigated for the ability to increase the ability to detect $PrP^{Sc}$ in brain homogenate as compared to the non-ionic detergent TRITON® X-100.

The plate diluent 1 base solution comprises, TRIZMA® Base (pH 8.3), N-Lauroyl Sarcosine detergent, Bovine Serum Albumin Solution, and Deionized water. The zwitterionic detergents used in the experiment include:
ZWITTERGENT® 3-8 (Zwitt 3-8): (n-Octyl-N,N-dimethyl-3-ammonio-1-propanesulfonate)
ZWITTERGENT® 3-10 (Zwitt 3-10): (n-Decyl-N,N-dimethyl-3-ammonio-1-propanesulfonate)
ZWITTERGENT® 3-12 (Zwitt 3-12): (n-Dodecyl-N,N-dimethyl-3-ammonio-1-propanesulfonate)
ZWITTERGENT® 3-14 (Zwitt 3-14): (n-tetradecyl-N,N-dimethyl-3-ammonio-1-propanesulfonate)
ZWITTERGENT® 3-16 (Zwitt 3-16): (n-Hexadecyl-N,N-dimethyl-3-ammonio-1-propanesulfonate)
EMPIGEN® BB: n-dodecyl-N,N-dimethylglycine
EMPIGEN® OB: Lauryldimethylamine oxide
NDSB 195: Dimethylethylammonium-1-propane sulfonate
NDSB 201: 3-(1-pyridino)-1-propane sulfonate
NDSB 221: 3-(1-methylpiperidium)-1-propane sulfonate
NDSB 256: Dimethylbenzylammonium-1-propane sulfonate The control was a non-ionic detergent additive: Triton®X-100: alkylaryl polyether alcohol.

TSE—EIA Assay:
Approved BSE EIA Test Kit components
Normal sheep brain homogenate (20% w/v)
Scrapie brain homogenate diluted into normal sheep brain homogenate@1:1500
Scrapie brain homogenate diluted into normal sheep brain homogenate@1:300
Scrapie brain homogenate diluted into normal sheep brain homogenate@1:40

Eleven zwitterionic detergents were added to a plate diluent base solution 1 at concentrations of 0.1%, 1.0%, & 10%. A control non-ionic detergent (TRITON® X-100) was also added to the plate diluent base at 5%, the amount previously determined to be the optimal concentration for this detergent. Each formulation of plate diluent 1 was mixed with the standard plate diluent 2 (2.5 mg/mL Trypsin; 1 mg/mL Dnase 1; 250 mM Tris HCl (pH 8.3) (final concentration in working plate diluent)) and then added to the 20% brain homogenate samples (100 ul brain homogenate to 25 ul working plate diluent). The sample/diluent mixture was added to a polyionic capture microtiter plate. Assays were performed according to standard BSE assay protocol using four samples as indicators: normal ovine brain homogenate and ovine scrapie brain homogenate that was diluted into normal sheep brain homogenate at 1:1500, 1:300, and 1:40 fold dilutions. A standard BSE EIA assay protocol was used. The sample was mixed with the working diluent while avoiding any bubbles. The diluted sample is added to the polyionic capture microplate along with the controls. The plate is covered and incubated for 2-3 hours. The plates are washed 6 times with 1× wash solution 1 (2.2 g/L Sodium Phosphate Monobasic, anhydrous; 11.9 g/L Sodium Phosphate Dibasic, anhydrous; 85 g/L Sodium Chloride; 10 g/L N-Lauroyl Sarcosine; deionized water). A conditioning buffer is added and the plates are covered and incubated for 10 minutes. The plates are washed 3 times with 1× wash solution 2 (2.2 g/L Sodium Phosphate Monobasic, anhydrous; 11.9 g/L Sodium Phosphate Dibasic, anhydrous; 85 g/L Sodium Chloride; 10 mL/L TWEEN® 20; deionized water). Conjugate (Conjugate Diluent:17.55 g/L Sodium Chloride; 0.22 g/L Sodium Phosphate Monobasic, anhydrous; 1.19 g/L Sodium Phosphate Dibasic, anhydrous; 0.5 mL/L Igepal CA-720; 2 mL/L 500 mM EDTA; 0.1%

Bovine Serum Albumin; 3 mL/L Blue Dye; Deionized water. Conjugate Concentrate Stock:12F10: HRPO Conjugate (final working concentration: 0.1-1 ug/ml); Stabilzyme conjugate stabilizer) is added to the plate. The plate is covered and incubated for 15 minutes. The reaction is stopped with HCl solution.

The plate is read at 450 nm (reference wavelength $A_{REF}$=620-650 nm). The cutoff is mean NC+0.120. For interpretation: if samples $A_{450}$-$A_{REF}$ is less than the cutoff the result is negative. If samples $A_{450}$-$A_{REF}$ is greater than or equal to the cutoff the result is initially reactive (retest in duplicate). If the duplicate retest mean $A_{450}$-$A_{REF}$ is greater or equal to the cutoff the sample is positive.

lowest with scrapie signal roughly equivalent or slightly lower than the control plate diluent 1 formulation.

Table 1 depicts the actual optical density values (OD) for testing the scrapie and normal ovine samples with the different plate diluent formulations. The test detergent OD values relative to the control detergent OD value for testing of the scrapie 1:300 sample are listed as an example of the increased signal obtained for the different zwitterionic detergents evaluated in this study. With only a few exceptions, the zwitterionic detergents result in a 2 to 2.8-fold increase in optical density for a positive sample with out increasing the signal on negative samples.

TABLE 1

| Plate Diluent | | Optical density of samples tested (450-650 nm) | | | | |
|---|---|---|---|---|---|---|
| Additives | | | Scrapie | Scrapie | Scrapie | OD test/OD control |
| Detergent | % | Normal Sheep | 1:1500 | 1:300 | 1:40 | (Scrapie 1:300) |
| Control (Triton X-100) | 0 (5%) | 0.032 | 0.086 | 0.207 | 0.998 | |
| Zwitt 3-8 | 0.1 | 0.034 | 0.185 | 0.479 | 2.359 | 2.31 |
| Zwitt 3-8 | 1 | 0.039 | 0.190 | 0.503 | 2.357 | 2.43 |
| Zwitt 3-8 | 10 | 0.035 | 0.144 | 0.396 | 1.946 | 1.91 |
| Zwitt 3-10 | 0.1 | 0.037 | 0.179 | 0.447 | 2.393 | 2.16 |
| Zwitt 3-10 | 1 | 0.041 | 0.191 | 0.514 | 2.592 | 2.48 |
| Zwitt 3-10 | 10 | 0.043 | 0.213 | 0.570 | 2.741 | 2.75 |
| Zwitt 3-12 | 0.1 | 0.036 | 0.171 | 0.428 | 2.192 | 2.07 |
| Zwitt 3-12 | 1 | 0.043 | 0.213 | 0.570 | 2.741 | 2.75 |
| Zwitt 3-12 | 10 | 0.038 | 0.182 | 0.480 | 2.525 | 2.32 |
| Zwitt 3-14 | 0.1 | 0.039 | 0.218 | 0.582 | 2.721 | 2.81 |
| Zwitt 3-14 | 1 | 0.037 | 0.190 | 0.530 | 2.311 | 2.56 |
| Zwitt 3-14 | 10 | 0.042 | 0.186 | 0.459 | 2.105 | 2.22 |
| Zwitt 3-16 | 0.1 | 0.36 | 0.181 | 0.499 | 2.173 | 2.41 |
| Zwitt 3-16 | 1 | 0.048 | 0.175 | 0.490 | 2.249 | 2.37 |
| Zwitt 3-16 | 10 | 0.051 | 0.160 | 0.397 | 2.041 | 1.92 |
| EmpigenOB | 0.1 | 0.040 | 0.164 | 0.420 | 2.398 | 2.03 |
| EmpigenOB | 1 | 0.035 | 0.103 | 0.264 | 1.470 | 1.28 |
| EmpigenOB | 10 | 0.036 | 0.059 | 0.113 | 0.627 | 0.55 |
| EmpigenBB | 0.1 | 0.039 | 0.185 | 0.510 | 2.394 | 2.46 |
| EmpigenBB | 1 | 0.039 | 0.163 | 0.402 | 2.280 | 1.94 |
| EmpigenBB | 10 | 0.031 | 0.079 | 0.164 | 0.924 | 0.79 |
| NDSB-195 | 0.1 | 0.036 | 0.172 | 0.436 | 2.105 | 2.11 |
| NDSB-195 | 1 | 0.036 | 0.178 | 0.455 | 2.186 | 2.2 |
| NDSB-195 | 10 | 0.038 | 0.184 | 0.463 | 2.280 | 2.24 |
| NDSB-201 | 0.1 | 0.037 | 0.182 | 0.453 | 2.282 | 2.19 |
| NDSB-201 | 1 | 0.038 | 0.182 | 0.468 | 2.323 | 2.26 |
| NDSB-201 | 10 | 0.037 | 0.188 | 0.472 | 2.337 | 2.28 |
| NDSB-221 | 0.1 | 0.038 | 0.186 | 0.505 | 2.488 | 2.44 |
| NDSB-221 | 1 | 0.038 | 0.177 | 0.448 | 2.066 | 2.16 |
| NDSB-221 | 10 | 0.040 | 0.202 | 0.530 | 2.364 | 2.56 |
| NDSB-256 | 0.1 | 0.036 | 0.180 | 0.482 | 2.202 | 2.33 |
| NDSB-256 | 1 | 0.042 | 0.224 | 0.568 | 2.469 | 2.74 |
| NDSB-256 | 10 | 0.041 | 0.196 | 0.541 | 2.350 | 2.61 |

FIGS. 1-11 show that in all cases, the addition of a zwitterionic detergent to the plate diluent 1 component at one or more concentrations doubled the positive signal in the three scrapie samples without marked increase in signal for the negative sample. In the case of the ZWITTERGENTS® (3-8, 3-12, 3-10, 3-14, & 3-16, FIGS. 5-9) and the NDSB's (195, 201, 221, & 256, FIGS. 12-15), the signal was nearly doubled in all cases regardless of the concentration of detergent used. In the case of the two EMPIGEN® detergents (EMPIGEN® OB & EMPIGEN® BB, FIGS. 10 and 11), the optimal results were obtained at the lower detergent concentration (0.1%). At EMPIGEN® concentrations of 1% and 10%, the positive scrapie signal declined relative to the 0.1% concentration. The 10% EMPIGEN® detergent concentrations were the All eleven zwitterionic detergents evaluated in plate diluent 1 of the TSE-EIA at a concentration of between 0.1-10% enhanced the $PrP^{Sc}$ specific signal by at least 2-fold as compared to the non-ionic TRITON® X-100 plate diluent formulation. This data demonstrates that a variety of zwitterionic detergents can be substituted into the TSE plate diluent 1 formulation and result in increased selective binding of $PrP^{Sc}$ by the polyionic capture material.

Example 3

The methodology of Example 2 was repeated using BSE samples. The results are shown in Table 2 and FIGS. 16-26.

TABLE 2

| Plate Diluent Additives | | Optical density of bovine samples tested (450-650 nm) | | | | OD test/OD control (BSE 1:100) |
|---|---|---|---|---|---|---|
| Detergent | % | Normal Bovine | BSE 1:218 | BSE 1:100 | BSE 1:55 | |
| Control (Triton X-100) | 0 (5%) | 0.043 | 0.117 | 0.234 | 0.410 | |
| Zwitt 3-8 | 0.1 | 0.038 | 0.172 | 0.414 | 0.759 | 1.77 |
| Zwitt 3-8 | 1 | 0.035 | 0.235 | 0.483 | 0.739 | 2.06 |
| Zwitt 3-8 | 10 | 0.035 | 0.255 | 0.528 | 0.929 | 2.26 |
| Zwitt 3-10 | 0.1 | 0.034 | 0.193 | 0.423 | 0.716 | 1.81 |
| Zwitt 3-10 | 1 | 0.036 | 0.178 | 0.426 | 0.768 | 1.82 |
| Zwitt 3-10 | 10 | 0.033 | 0.232 | 0.496 | 0.844 | 2.12 |
| Zwitt 3-12 | 0.1 | 0.036 | 0.169 | 0.392 | 0.676 | 1.68 |
| Zwitt 3-12 | 1 | 0.040 | 0.270 | 0.662 | 1.075 | 2.83 |
| Zwitt 3-12 | 10 | 0.040 | 0.280 | 0.573 | 0.962 | 2.45 |
| Zwitt 3-14 | 0.1 | 0.048 | 0.219 | 0.487 | 0.705 | 2.08 |
| Zwitt 3-14 | 1 | 0.047 | 0.337 | 0.705 | 1.195 | 3.01 |
| Zwitt 3-14 | 10 | 0.037 | 0.413 | 0.827 | 1.242 | 3.53 |
| Zwitt 3-16 | 0.1 | 0.041 | 0.181 | 0.456 | 0.735 | 1.95 |
| Zwitt 3-16 | 1 | 0.046 | 0.339 | 0.722 | 1.157 | 3.09 |
| Zwitt 3-16 | 10 | 0.047 | 0.594 | 1.130 | 1.601 | 4.83 |
| EmpigenOB | 0.1 | 0.051 | 0.168 | 0.380 | 0.734 | 1.62 |
| EmpigenOB | 1 | 0.038 | 0.204 | 0.367 | 0.615 | 1.57 |
| EmpigenOB | 10 | 0.040 | 0.139 | 0.312 | 0.530 | 1.33 |
| EmpigenBB | 0.1 | 0.035 | 0.176 | 0.380 | 0.755 | 1.62 |
| EmpigenBB | 1 | 0.035 | 0.142 | 0.281 | 0.490 | 1.20 |
| EmpigenBB | 10 | 0.035 | 0.144 | 0.233 | 0.369 | 1.00 |
| NDSB-195 | 0.1 | 0.037 | 0.185 | 0.400 | 0.705 | 1.71 |
| NDSB-195 | 1 | 0.047 | 0.192 | 0.428 | 0.692 | 1.83 |
| NDSB-195 | 10 | 0.038 | 0.174 | 0.374 | 0.740 | 1.60 |
| NDSB-201 | 0.1 | 0.046 | 0.183 | 0.396 | 0.662 | 1.69 |
| NDSB-201 | 1 | 0.034 | 0.180 | 0.398 | 0.743 | 1.70 |
| NDSB-201 | 10 | 0.049 | 0.193 | 0.405 | 0.687 | 1.73 |
| NDSB-221 | 0.1 | 0.034 | 0.179 | 0.364 | 0.729 | 1.56 |
| NDSB-221 | 1 | 0.042 | 0.169 | 0.339 | 0.712 | 1.45 |
| NDSB-221 | 10 | 0.040 | 0.185 | 0.431 | 0.835 | 1.84 |
| NDSB-256 | 0.1 | 0.047 | 0.201 | 0.422 | 0.746 | 1.80 |
| NDSB-256 | 1 | 0.041 | 0.204 | 0.450 | 0.759 | 1.92 |
| NDSB-256 | 10 | 0.048 | 0.183 | 0.406 | 0.824 | 1.74 |

What is claimed is:

1. A method for selective binding of an aggregating abnormal form of a prion protein in the presence of a non-aggregating normal form of the prion protein, comprising contacting, under selective binding conditions, brain tissue suspected of comprising the aggregating abnormal form and the non-aggregating normal form of the prion protein with a polyionic material having a binding avidity for the abnormal aggregating form of the prion protein, a zwitterionic agent, and a discriminating agent, wherein the aggregating abnormal form of the prion protein selectively binds to the polyionic material.

2. The method of claim 1 wherein the polyionic material is protease resistant.

3. The method of claim 1 wherein the polyionic material is a polyanionic material having a multiplicity of anionic groups or a polycationic material having a multiplicity of cationic groups.

4. The method of claim 3 wherein the polyionic material has a multiplicity of anionic groups that are sulphate, carboxyl or phosphate groups or a multiplicity of cationic groups that are amino groups, imine groups or quaternary ammonium groups.

5. The method of claim 4 wherein the discriminating agent has a lesser density of anionic groups than the polyionic material.

6. The method of claim 1 wherein the discriminating agent is an anionic detergent.

7. The method of claim 1 wherein the discriminating agent is an amino acid amide of a fatty acid.

8. The method of claim 1 wherein the discriminating agent is laurylsarcosine.

9. The method of claim 1 wherein the aggregated abnormal form of the prion protein that is selectively bound to the polyionic material is captured with an immobilized capture agent.

10. The method of claim 9 wherein the capture agent is an antibody specific for the aggregated abnormal form of the prion protein.

11. The method of claim 1 wherein the polyionic material which is selectively bound to the aggregated abnormal form of the prion protein is captured with an immobilized capture agent.

12. The method of claim 11 wherein the capture agent is a lectin or an antibody.

13. The method of claim 1 wherein the selective binding conditions comprise a pH from about 8 to about 9.

14. The method of claim 1 wherein the selective binding conditions comprise a pH from about 8.2 to about 8.6.

15. The method of claim 11 wherein the polyionic material comprises a selectively bindable tag moiety and the capture agent selectively binds to the tag moiety.

16. The method of claim 9 wherein the aggregated abnormal form of the prion protein comprises a selectively bindable tag moiety and the capture agent selectively binds to the tag moiety.

17. The method of claim 1 wherein the polyionic material is immobilized to a solid support material prior to contacting the brain tissue.

18. The method of claim 17 wherein the solid support material has the polyionic material coated thereon.

19. The method of claim 17 wherein the polyionic material comprises a selectively bindable tag moiety and is immobilized to the solid support material via the tag moiety.

20. The method of claim 19 wherein the bindable tag moiety is biotin, fluorescein, dinitrophenol, digoxyrenin, a nucleic acid or nucleic acid analogue sequence or (His) 6.

21. The method of claim 15 wherein the bindable tag moiety is biotin, fluorescein, dinitrophenol, digoxyrenin, a nucleic acid or nucleic acid analogue sequence or (His) 6.

22. The method of claim 1 wherein the polyionic material is a solid that provides a surface having said binding avidity.

23. The method of claim 1 wherein the zwitterionic agent comprises a zwitterionic detergent.

24. The method of claim 1 wherein the zwitterionic agent is selected from the group consisting of n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, n-tetradecyl-N,N-dimethyl-3-ammonio-1-propanesulfonate, n-Hexadecyl-N,N-dimethyl-3-ammonio-1-propanesulfonate, a sulfobetaine, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate n-dodecyl-N,N-dimethylglycine, lauryldimethylamine oxide, and combinations thereof.

25. The method of claim 1 wherein the zwitterionic agent comprises a sulfobetaine.

26. The method of claim 1 wherein the zwitterionic agent comprises a sulfonate group or a carboxyl group.

27. A method of determining presence or absence of an abnormal aggregating form of a prion protein in a brain tissue sample in the presence of the non-aggregating normal form of the prion protein, comprising, contacting under selective binding conditions, brain tissue suspected of comprising the aggregating abnormal form of the prion protein and the non-aggregating normal form of the prion protein with a polyionic material having a binding avidity for the abnormal aggregating form of the prion protein, a discriminating agent and a zwitterionic agent; and determining the presence or absence of the abnormal aggregating form of the prion protein bound to the polyionic material.

28. The method of claim 27, wherein an amount of the abnormal aggregating form of the prion protein is determined.

29. The method of claim 27 wherein determining the presence or absence of the abnormal aggregating form of the prion protein bound to the polyionic material is qualitatively or quantitatively determined by conducting an immunoassay for the aggregating form of the prion protein.

30. The method of claim 27 wherein the abnormal aggregated form of the prion protein is $PrP^{Sc}$ and the non-aggregated normal form of the prion protein is $PrP^c$.

31. The method of claim 1 wherein the abnormal aggregated form of the prion protein is $PrP^{Sc}$ and the non-aggregated normal form of the prion protein is $PrP^c$.

32. The method of claim 27 wherein the zwitterionic agent comprises a zwitterionic detergent.

33. The method of claim 27 wherein the zwitterionic agent is selected from the group consisting of n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, n-tetradecyl-N,N-dimethyl-3-ammonio-1-propanesulfonate, n-Hexadecyl-N,N-dimethyl-3-ammonio-1-propanesulfonate, a sulfobetaine, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate n-dodecyl-N,N-dimethylglycine, lauryldimethylamine oxide, and combinations thereof.

34. The method of claim 27 wherein the zwitterionic agent comprises a sulfobetaine.

35. The method of claim 27 wherein the zwitterionic agent comprises a sulfonate group or a carboxyl group.

* * * * *

UNITED STATES PATENT AND TRADEMARK OFFICE
CERTIFICATE OF CORRECTION

PATENT NO. : 7,659,079 B2  Page 1 of 1
APPLICATION NO. : 11/099128
DATED : February 9, 2010
INVENTOR(S) : Estey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this

Thirtieth Day of November, 2010

David J. Kappos
*Director of the United States Patent and Trademark Office*